(12) United States Patent
Goertler et al.

(10) Patent No.: US 8,595,553 B2
(45) Date of Patent: Nov. 26, 2013

(54) ERROR PATTERN IDENTIFICATION IN AN INSTALLED BASE OF SYSTEMS

(75) Inventors: Georg Goertler, Baiersdorf (DE); Robert Bertossi, Erlangen (DE); Harald Schultz, Altdorf (DE); Bastian Rackow, Herzogenaurach (DE); Norbert Engels, Erlangen (DE); Peter Haeuser, Effeltrich (DE)

(73) Assignee: Siemens Aktiengesellschaft, München (DE)

( * ) Notice: Subject to any disclaimer, the term of this patent is extended or adjusted under 35 U.S.C. 154(b) by 231 days.

(21) Appl. No.: 12/793,247

(22) Filed: Jun. 3, 2010

(65) Prior Publication Data

US 2011/0302461 A1 Dec. 8, 2011

(51) Int. Cl.
*G06F 11/00* (2006.01)

(52) U.S. Cl.
USPC ............. 714/26; 714/4.3; 714/4.4; 714/25

(58) Field of Classification Search
USPC ........................ 714/4.3, 4.4, 25, 26
See application file for complete search history.

(56) References Cited

U.S. PATENT DOCUMENTS

| | | | | |
|---|---|---|---|---|
| 4,633,467 A * | 12/1986 | Abel et al. | | 714/45 |
| 4,922,491 A * | 5/1990 | Coale | | 714/26 |
| 5,210,704 A * | 5/1993 | Husseiny | | 702/34 |
| 5,253,184 A * | 10/1993 | Kleinschnitz | | 702/184 |
| 5,394,543 A * | 2/1995 | Hill et al. | | 714/26 |
| 5,448,722 A * | 9/1995 | Lynne et al. | | 706/49 |
| 5,463,768 A * | 10/1995 | Cuddihy et al. | | 714/37 |
| 5,528,516 A * | 6/1996 | Yemini et al. | | 702/181 |
| 5,568,491 A * | 10/1996 | Beal et al. | | 714/746 |
| 6,105,149 A * | 8/2000 | Bonissone et al. | | 714/26 |
| 6,260,048 B1 * | 7/2001 | Carpenter et al. | | 1/1 |
| 6,675,323 B2 * | 1/2004 | Bartenstein et al. | | 714/29 |
| 6,745,151 B2 * | 6/2004 | Marko et al. | | 702/182 |
| 6,907,545 B2 * | 6/2005 | Ramadei et al. | | 714/25 |
| 7,062,670 B1 * | 6/2006 | Larsson et al. | | 714/4.2 |
| 7,082,554 B2 * | 7/2006 | Wilson et al. | | 714/43 |
| 7,379,846 B1 * | 5/2008 | Williams et al. | | 702/185 |
| 7,506,195 B2 * | 3/2009 | Takahashi et al. | | 714/4.4 |
| 7,757,122 B2 * | 7/2010 | Hikita et al. | | 714/27 |
| 7,860,768 B2 * | 12/2010 | Herter et al. | | 705/35 |
| 7,890,813 B2 * | 2/2011 | Usynin et al. | | 714/45 |
| 8,032,330 B2 * | 10/2011 | Makela et al. | | 702/185 |
| 8,161,323 B2 * | 4/2012 | Kuchibhotla et al. | | 714/25 |
| 2004/0128583 A1 * | 7/2004 | Iulo et al. | | 714/25 |
| 2005/0172162 A1 * | 8/2005 | Takahashi et al. | | 714/4 |
| 2007/0168753 A1 * | 7/2007 | Herter et al. | | 714/42 |
| 2007/0226540 A1 * | 9/2007 | Konieczny | | 714/26 |
| 2009/0106589 A1 * | 4/2009 | Ramacher et al. | | 714/25 |

* cited by examiner

*Primary Examiner* — Joshua P Lottich
(74) *Attorney, Agent, or Firm* — Lempia Semmerfield Katz LLC (57) ABSTRACT

A system and method of servicing a group of similar types of equipment that maybe installed at geographically separated locations is described. The method makes use of error messages produced by the equipment and service requests received by a servicing center. Data mining techniques are used to establish error patterns associated with specific failure modes so that future error messages may be processed to determine if an identified failure mode has occurred. This will enable the efficient dispatch of spare parts and service personnel to the location where the failure has occurred.

12 Claims, 4 Drawing Sheets

Material ID

ERROR PATTERN IDENTIFICATION IN AN INSTALLED BASE OF SYSTEMS

TECHNICAL FIELD

The present application may relate to a system and method of determining a response to a failure of equipment at geographically separate locations.

BACKGROUND

Complex systems, deployed in geographically dispersed locations, such as magnetic resonance imaging (MRI), computed tomography (CT) and other industrial and medical systems, are expensive to maintain. The diagnosis of component and subsystem failures by a technician, or by manual analysis of error reports; is both costly and time consuming. Often the great complexity of such systems means that the error reports describe error states but do not permit a direct conclusion about the defective component. That is, in some way the system has failed to perform properly, yet the error reported does not correspond to a uniquely identified component to be replaced, repaired, calibrated, or the like, so as to restore the system to a valid operational state.

Resolving reported errors often requires dispatching a technician to the site so as to perform special testing routines so as to attempt to solve the problem. However, such test routines are time consuming; they may diagnose a failure for which a spare part is not available at the equipment site, and may therefore require further time to acquire the spare part and a subsequent additional technician visit to perform the repair. In other instances, an on-site test routine may not be feasible for a particular failure type, such as in a closed-loop portion of the system, where additional test fixtures may be needed. These are normally only available during the development phase of the project.

The great complexity of, for example, MRI systems, means that the error reports or error states do not permit a direct conclusion about the defective component causing the failure. This typically leads to high consumption of spare parts where such parts are replaced without the curing of the defect, longer searches for errors, and a high proportion of returned goods that are not defective.

When an error is reported by a user, a support engineer at a central, regional, or local service center may attempt to find a suitable preliminary explanation, on the basis of the error reports, so as to dispatch the appropriate spare part and service technician. However, due to the above-described problems, this preliminary diagnosis often cannot unambiguously identify a defective part.

BRIEF SUMMARY

A system for managing the servicing of a geographically separated installed base of equipment is described, including an interface for receiving error reports from the equipment; a processor configured to store the error reports as a data base on a non-volatile medium; and, a data miner configured to process the error reports in the data base and to formulate an error pattern rule indicating an error report to be the subject of a specific service event. The processor is operative to compare a currently received error report with the error pattern rule and output a notification of the specific service event when a match between the error report and the error pattern rule occurs.

In an aspect, a method of servicing geographically dispersed equipment is disclosed, including the steps of receiving error reports from a plurality of geographically dispersed equipment; storing the error reports in a non-volatile data base; operating a computer configured to perform data mining of the error reports to produce error pattern rules indicative of a specific failure type; comparing a subsequent error report received from the equipment with the error pattern rules to determine when a match between the error report and a rule of the error pattern rules occurs; and, outputting a report when a match occurs, the report including a specific equipment of the geographically dispersed equipment and the specific failure type associated with the error pattern rule that has been matched.

In yet another aspect, a computer program product includes instructions stored on a computer-readable medium, the instructions capable of configuring a computer to receive error reports from a plurality of geographically dispersed equipment; to store the error reports in a non-volatile data base; to perform data mining of the error reports to produce error pattern rules indicative of a specific failure type; to compare a subsequent error report received from the equipment with the error pattern rules to determine when a match between the error report and a rule of the error pattern rules occurs; and, to output a report when a match occurs, the report including a specific equipment of the geographically dispersed equipment and the specific failure type associated with the error pattern rule that has been matched.

DETAILED DESCRIPTION

Exemplary embodiments may be better understood with reference to the drawings. Like numbered elements in the same or different drawings perform equivalent functions.

In the interest of clarity, not all the routine features of the examples herein are described. It will of course be appreciated that in the development of any such actual implementation, numerous implementation-specific decisions must be made to achieve a developers' specific goals, such as consideration of system and business related constraints, and that these goals will vary from one implementation to another.

Systems may be considered to have three phases of a lifetime; development, deployment and support. During the development of a system, the design phase may consider operational requirements and specifications, and may also consider the subsequent servicing and quality control aspects of the deployed system. In particular, sensors or software routines may be developed so as to ensure the proper operation of the system and to identify and report anomalies in the performance of the system. These anomalies may result from aging of components, and require recalibration or replacement of the components, or from the failure of a component. During the development phase reports generated by the system may be collected so as to provide a preliminary basis for a servicing plan. By daily collection of system reports, a correspondingly comprehensive database of these reports is generated.

A modern computer controlled and monitored complex system may provide a data base of information suitable for applying data mining techniques. These systems may contain many sensors and computer-controlled and monitored devices, so the information needed for decisions may be acquired. Particularly, where a plurality of the same or similar systems are deployed over a wide geographical area, and such systems have the ability to report error or failure conditions either immediately, or as a batch process to a central analysis facility, the reports may be suitable for improving the servicing and serviceability of such systems.

In such complex systems, the variety of sensors, parameter measurements, and replaceable components and failure modes may far exceed the ability of manual evaluation, even where simple statistical methods are used. That is, for example, the correspondence between error or failure messages and specific replaceable hardware components, recalibration or adjustment requirements, and the like may be sufficiently complex that a simple analysis would be inadequate to uncover the relationships that exist in the physical world.

Data mining is ordinarily used so as to uncover patterns of behavior in human and business activities where a large amount of data is processed, using a variety of algorithms so as to attempt to uncover patterns of behavior. Such patterns may be used for business purposes such as predicting demand for a type of product, estimating the response to an advertizing or direct mail campaign, or the like. These are examples where the patterns do not have an a priori deterministic character. The results are therefore couched in terms of a probability that something may occur.

While the probability of a specific failure or required adjustment may be a matter of experience based on actual events, a relationship between specific reported events or process failures, or the like, and a specific hardware component failure or a specific adjustment to be made may be uncovered by appropriately mining the data base of experience with failures and adjustments, and the corresponding data base of reports of events. Such relationships, where they exist and can be identified by data mining, provide for increased efficiency in servicing equipment, more efficient use of a spare parts inventory, and proactive servicing so as to repair or adjust the system prior to an actual failure. Of course, some components of the system may not show such relationships. Often these are passive mechanical components, such as a patient cushion or a mechanical housing. Generally, such components are obviously candidates for replacement on visual inspection or on an elapsed time basis, or have such a low failure rate as to have a minimal effect on the overall cost of ownership.

Development of a suitable model for improving the servicing of the system may proceed by dividing the existing data base into several portions. A first portion may be used to develop the model to be used in future actions, and the second portion may be used to validate the model.

Development of the model may begin during the development of the system, and continue to gain experience once the system has been deployed. The learning experience may uncover less probable events as the temporal and physical extent of the data base increases, and may increase the confidence of the identification of a relationship where the relationship is complex or has no apparent physical basis. Such relationships may then be investigated by other means for validation.

During the development phase of a system, error reports may be collected and analyzed to identify failed components and the conclusiveness of the error reports is improved during the development process. However, not all the relevant error reports can be tested, and the detection of the defective components, particularly in the operation of deployed systems, may be limited.

Once the system has been deployed, an in-service database (IPB) may be established where all the service-relevant information is available: for example, exchanged spare parts, error descriptions, start and end of error correction, and the like.

The in-service data base may be analyzed so as to determine whether there are identifiable error patterns that may be correlated with each other (error reports, warning messages, procedure aborts) so that an error pattern may be generated. By associating such error patterns with actual diagnosed failures, represented by a material failure, or the need for a specific calibration action, the error patterns may be linked with specific servicing actions (specific spare parts, and specific calibrations or adjustments). The precision of conclusiveness of the material patterns may be optimized iteratively with the aid of test data (training data and non-training data). A further advantage is that predictive service is made possible. Based on a daily transfer of all the reports to a central database, regular pattern analyses may be performed and events generated that make predictive service possible.

After the patterns have been identified and the analysis technique validated, the data mining operation may proceed in an automated fashion to incorporate new reports as they are received, or on a batch basis. The received reports may also be compared against the results of the data mining operations previously performed so as to evaluate the individual report for correspondence with an indicated response (service call, adjustment, replacement of a component, or the like) based on the established identifications and patterns.

Such a servicing strategy may assist in situations where the testing that a service technician may perform may be limited by the nature of the test equipment or the functioning of the system. Even using a special test software routine, which itself may be time consuming, and may need an on-site visit, failures of components in a closed-loop portion of the system may not be resolvable without speculative replacement of failed modules. While this may be mitigated by replacing the module in the loop having the highest experiential failure rate, the variety of spare parts which the service technician may need to bring to the service call may be excessive.

Failures may be reported to a service center manually, by system-generated messages transmitted as they occur, or by batch transfer of messages originating during a specific time period. For simplicity of discussion, this description follows a path where the event messages have been generated by an individual system, transmitted to a service center, and entered into the service message data base by any of the above methods. Manual data entry is also possible, although such manual data entry may be less common in future.

A failure may include hardware failures, adjustment or calibration errors, or failure to normally complete a process. Some of these failures may require replacement of a component, others may require an adjustment of recalibration of an aspect of the system, while yet others may have uncovered a software bug, or an operational procedure that is being incorrectly performed. The received event message for a reported failure or problem is compared with the identified relationships based on the model and the pre-existing data.

Where the event report has been previously associated in the model with a specific response, then that response may be provided. Other reports that are not so identified may be analyzed manually, referred to engineering for further development, or serve as the basis for revision of software or operating manual. Thus, a large number of the error reports may be assessed on the basis of the experience data base rather than depending on a service technician. The results would be more consistent, would provide a faster response time, and would minimize unproductive service visits and consumption of spare parts.

Where the error reports are sent to the service center on a regular basis, certain error reports may have a predictive nature. That is, a particular error report may be associated with a failure that is highly likely to occur at a future time. Depending on the nature of the failure, the advance warning time, and the like, such servicing may be performed as preventive maintenance, so as to anticipate the need.

While the development of the techniques described herein is based on data collected and analyzed for a Magnetic Resonance Imaging (MRI) system, the approach described herein may be applied effectively to systems for which a structured error reporting process exists. Such reports may be in electronic form, and may be automatically generated. However, this does not preclude the use of such reports where the reports are manually generated. During the development phase of a system, error reports are collected, so as to develop a comprehensive data base of such reports. Similarly, after deployment of the system, an in-service data base is developed where service-relevant information is available from event reports (exchanged spare parts, error descriptions, start and end of error correction, and the like). The individual system reports (error reports, warnings, information, and the like) are correlated with one another such that error patterns can be generated.

By correlating the service reports (historical training data) with the reports from the systems, material patterns are created that point to individual spare parts (material numbers) or spare part groups (material groups). The precision of conclusiveness of the identification of the material patterns may be optimized iteratively with the aid of test data (training data and non-training data). Thus, based on the report history of a system, a decision can be made as to which material has to be replaced. Such a determination may be made at the service center, permitting more efficient dispatch of service technicians and replacement parts.

The combination of hardware and software to accomplish the tasks described herein may be termed a system. The instructions for implementing processes of the system and method may be provided on computer-readable storage media or memories, such as a cache, buffer, RAM, removable media, hard drive or other computer readable storage media. Computer readable storage media include various types of volatile and nonvolatile storage media. The functions, acts or tasks illustrated or described herein may be executed in response to one or more sets of instructions stored in or on computer readable storage media. The functions, acts or tasks may be independent of the particular type of instruction set, storage media, processor or processing strategy and may be performed by software, hardware, integrated circuits, firmware, micro code and the like, operating alone or in combination. Some aspects of the functions, acts, or tasks may be performed by dedicated hardware, or manually by an operator.

The instructions may be stored on a removable media device for reading by local or remote systems. In other embodiments, the instructions may be stored in a remote location for transfer through a computer network, a local or wide area network, by wireless techniques, or over telephone lines and be stored for local execution by the computer or system. In yet other embodiments, the instructions are stored within a given computer, system, or device.

Communications between the devices, the system, subsystems, and applications may be by the use of either wired or wireless connections. Such communications may include the use of a local area network (LAN), a wide area network (WAN) such as the Internet, the public switched telephone network (PTSN), or such other equivalent systems that exist or may subsequently be developed. Wireless communication may include, audio, radio, lightwave or other technique not requiring a physical connection between a transmitting device and a corresponding receiving device. While the communication may be described as being from a transmitter to a receiver, this does not exclude the reverse path, and a wireless communications device may include both transmitting and receiving functions. Wireless communication makes use of electronic hardware and antennas to radiate electromagnetic radiation which may be received by suitable antennas and electronic hardware and processed to obtain the information that has been transmitted.

Figure 1:
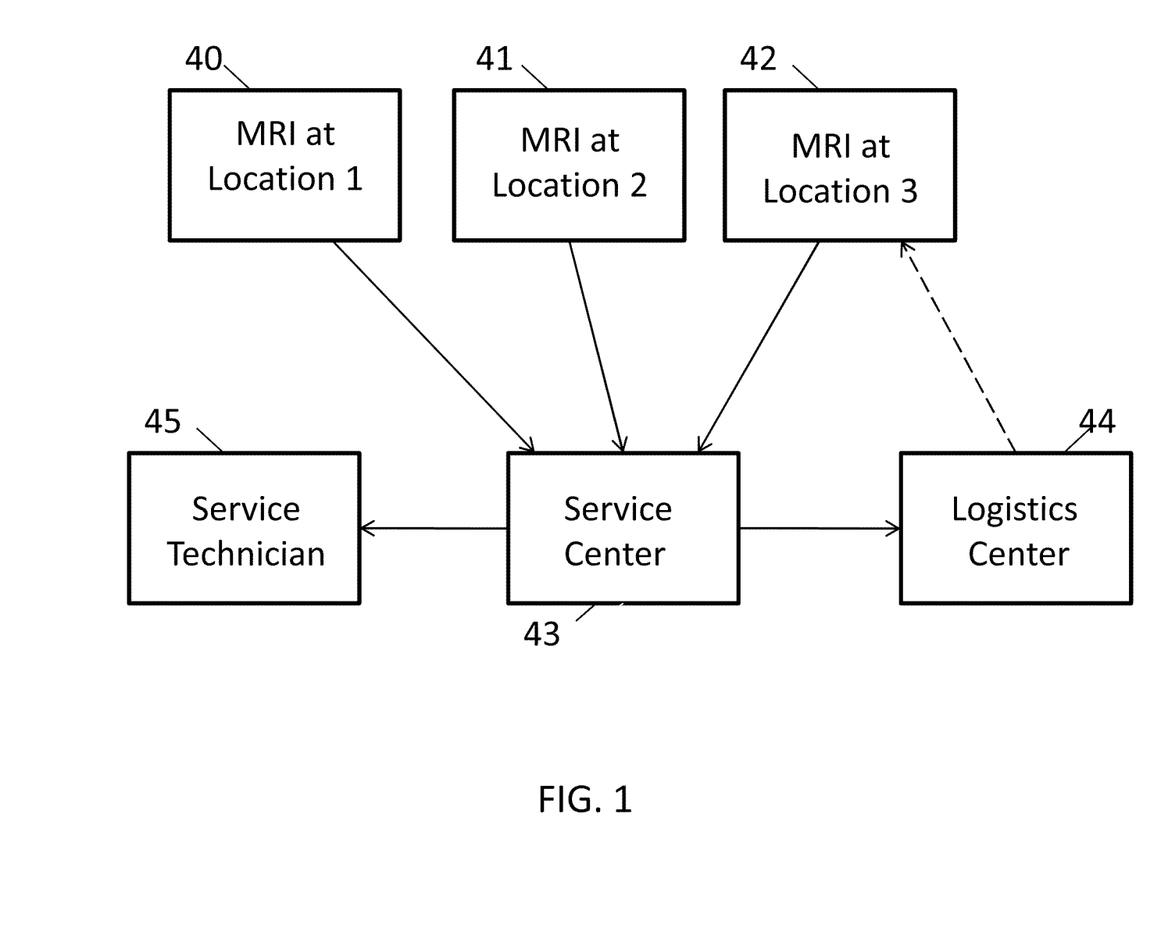
FIG. 1 shows an example of a distributed group of systems being serviced from a remote location.

An example of a distributed installed base of equipment being supported by a remotely located service center and a remotely located logistics center is shown in FIG. 1. In this example, a plurality of MRI systems 40, 41, 42 are located at geographically separated locations. The MRI systems may be of the same type or of differing types or versions. A plurality of different MRI types may be deployed at the same location, or the MRI systems may be of the same type but different versions. The systems may share some common repair parts, but this is not a requirement. Each of the MRI systems 40-42, or the corresponding facility location, is in communications with a service center 43, which is generally located separately from the MRI systems. The MRI systems are typically located at a hospital or specialized diagnostic facility, while the service center 43 may be located wherever convenient from a business viewpoint. The service center and the MRI locations are connected by a communications network, which may be the Internet, a private network, or the like, so that messages generated by either the MRI locations or the service center may be exchanged. Such messages may include both automatically generated messages, associated with the operation of the MRI systems, or be manually generated requests for service, for such service operations that are not within the scope of the equipment operating or diagnostic programs. The service center 43, communicates with a logistics center 44 where replacement parts are available for dispatch to the MRI locations. The service center may also communicate with a service technician 45, for purpose of coordinating service activities with the nature of the service request and the availability of a replacement part. Communications with the service technician may be voice over conventional lines, the Internet, or a virtual private network, or the like, or by similar digital or analog communications.

The efficiency of such a distributed servicing operation depends on the accuracy with which the service request or error message can be interpreted to identify the failed system component and the skills of the technician who is dispatched to perform the service. To the extent that these operations can be performed accurately, the number of service calls, the duration of the outage, and the concomitant cost and inconvenience may be reduced. With a large number of systems, and versions thereof, and the constantly changing mix of deployed equipment, this task may be difficult to perform efficiently.

The experience that may be gained during the development of each system, that relates observed failures, and failure error reports to specific failed modules may be used to construct rules to identify the module to be replaced based on reported failures from subsequently deployed systems. However, not all such errors may occur during the development phase, as only a small population of equipment would be available for determining the relationship between module failures and error reports. When a large number of systems have been deployed, additional error messages and failures may occur, and the correlations between the error messages and other diagnostic information and the actual failed module may not be known. Such failure data may also be available during production testing.

Collecting analysis data and failure reports, and information on the specific module or modules that were replaced to restore the equipment to a proper operating state may provide further information for managing the servicing operation. The information may be developed using data mining techniques.

A development project for analyzing the error messages and resultant repair actions in response to service requests was undertaken to develop this approach to system level computer-aided learning and decision making for servicing deployed equipment.

The development project used here as an example utilizes experiential patterns resulting from analyzing error event logs or other kinds of logs produced by computers used in MRI machines, to determine which materials need to be replaced, when customer requests customer service with an equipment problem. That is, the spare part that is needed is determined based on the received error messages. The error messages are compared with an error pattern filter that was created by data mining of data from a preexisting data base. The data base may continue to be updated.

An identified error pattern is a specific combination of events (error messages, parts replaced, and the like) extracted from the data base. In this example, the analysis was restricted to patterns of events that occur during aborted MRI measurements. However this approach may also be used to analyze measurement preparation phases, initialization of the scanner or image processor or even whole days of operation as a working machine. Since the present example study was limited to a particular state of operation of the MRI system, not all of the hardware failures would be manifest in the data. However, by extending the analysis to a broader scope of the operation of the system, additional failures should be observable. The technique may be applicable to any type of system where failures occur and where information relating to the effects of the failure are available.

Two variants of pattern generation are defined. The first variant is the "Metric Pattern", which is based on metric pattern used in an installed base monitoring (IBM) process to calculate several key performance indicators (KPI). This is a somewhat heuristic approach. The patterns are created by analyzing aborted measurements and generally analyzing one specific error. The patterns may be refined by consideration of other errors, so that each finished pattern points to a specific faulty material with a high probability. One would like to achieve a one-to-one relationship between an error and a faulty component. The second variant is the "Error Pattern". This type of pattern is derived directly from failure events during aborted measurements and modules replaced, without consideration of actual failure that occurred. That is, the results are based on operating experience. The data acquisition, the data processing and the algorithm for the generation of pattern files are described. In order to better understand the process, a number of the further assumptions, and the terminology used, is first explained. The terminology, the assumptions, and the like, used in the demonstration project are not intended to be construed as limitations of the scope and use of the resultant system, but are helpful in providing context and in better understanding the concepts disclosed.

All date values used (such as DownTimeStart, DownTimeEnd) are understood to be dates and not date times. That is, when a notification started in the afternoon of Aug. 12, 2009, DownTimeStart is set to Aug. 12, 2009 00:00:00. "DownTimeStart+1" therefore means Aug. 12, 2009 24:00:00. This is an artificially enforced granularity limitation for simplicity in analysis; however, more fine grained temporal analysis of the data may be useful for certain situations where sufficient data is available.

The following terms are used as a convenient nomenclature for describing the data:

Nice Notification

Nice IPB (Installed Product Data Base) Notifications are notifications, for which one can be reasonably certain that the exchange of one and only one type of material accounts for possible changes in the behavior of the MRI system. A Nice Notification satisfies the following conditions:

NotificationType='reactive Service;'

The calculated DownTimeEnd is set (is not NULL);

The overall downtime does not exceed 30 days;

At least one material was exchanged: (sum(Movement TypeFlag)>=1); and

Only materials of one material identification number were exchanged.

Good Patternhit

A Patternhit is considered good for a Notification N if the error report that has caused the Patternhit was corrected by exchanging the material identified in the in the Notification for a spare version thereof. A Patternhit X is a Good Patternhit for notification N, if the following conditions are satisfied:

There was a patternhit X shortly before notification N was opened: ([DownTimeStart−3, DownTimeStart+1]); and There was no patternhit X for 30 days after the end of notification N: ([calculatedDTE+1, calculatedDTE+31])

Correct Good Patternhit

A Correct Good Patternhit is a Good Patternhit and the material of the Notification is the same as the material for which the pattern was written.

Good Error

An error report is considered good for a notification if the error was removed by exchanging the material in the notification. An error report X is a good error report for notification N, if the following conditions are satisfied:

An error report X occurred during an aborted measurement shortly before notification N was opened: ([DownTimeStart−3, DownTimeStart+1]); and No error report X occurred during an aborted measurement for 30 days after the end of notification N: ([calculatedDTE+1, calculatedDTE+31]).

The data were processed, analyzed and displayed using a data mining tool known as RapidMiner, which is an open-source development project available for downloading from the Internet that supports various data mining algorithms and visualization methods for both input and output data. Other comparable data mining tools are commercially available.

Variant 1 and Variant 2 were implemented and their performance compared. Variant 1 used pre-calculated IBM (Installed Base Monitoring) metric pattern hits correlated with the IPB notifications (error, event, or status reports). Herein, terms such as error, error report, status report, stop code and the like are used. Other terms may be used by different manufacturers and service organizations. The use of any of these terms is not intended to exclude other equivalent descriptions that are reported by a user of a system. Data mining methods are used with the MRI error event logs to create material metric pattern.

Variant 2 correlated the IPB notifications directly with the aborted MRI measurements and the module replacements resulting in the notifications. This correlation data was used with data mining methods and the complete MRI event data logs to create a material error pattern. Both types of pattern were then input to an analysis program that determines Patternhits. Data-base-compatible tables were used to collate and analyze data from the installed base of MRI systems. All the tables were derived from the IPB reports and were updated with current data from deployed MRI systems on a daily or weekly basis.

An IPB Notification table contained data for customer service notifications from the IPB database. Relevant data for one Notification may be, for example: DownTimeStart, DownTimeEnd, the specific MRI machine, or the model and version type, and which materials were used in performing the repair. The DownTimeEnd is the date, when a Notification was closed. The MRI Event Log table contains the event log entries that were sent by MRI systems in the field. The IBM Metric Patternhits table was calculated on a regular basis using the MRI event logs. The MRI Measurements table has the MRI measurements that were started on MRI systems that send data to the IBM. One row contains the serial number of the MRI system, the event log entry that starts the measurement and the event log entry that stops the measurement.

Figure 2:
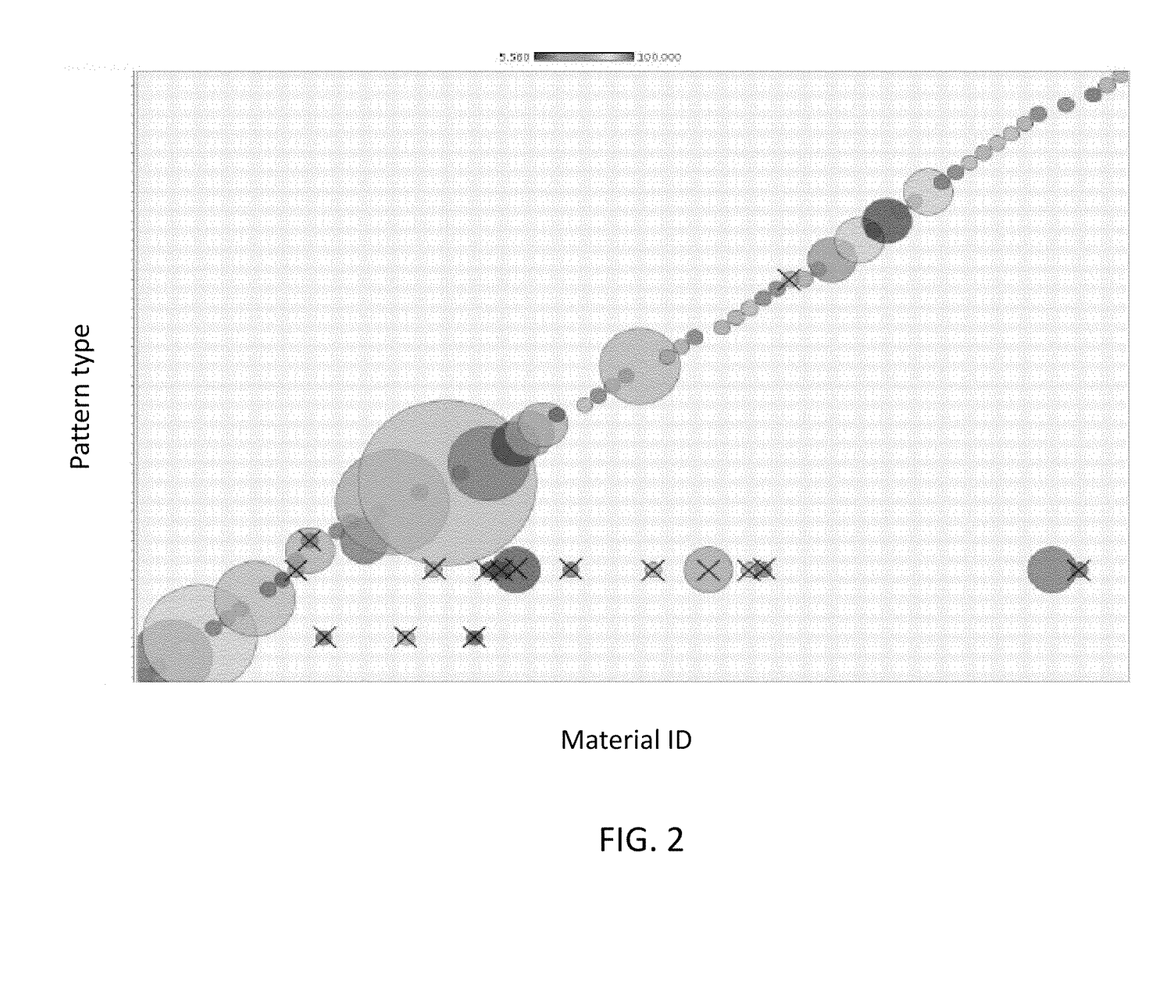
FIG. 2 shows a bubble chart of the relationship between error message patterns and failed modules based on training with experiential data.

FIG. 2 is a flow diagram of the process used to establish the Variant 1 Metric Pattern and the Variant 1 Error Pattern. The analysis to refine IBM Metric Pattern starts with determining all Good Pattern Hits for every Nice Notification in the IPB database. For this, the two tables are joined using, for example, SQL software, and then all (Notification, Material, Pattern) combinations, where the pattern had a Good Hit for the Notification are extracted. Then, the table was grouped by materials identification to get an overview of which pattern maybe a good indicator for a certain failed material. An excerpt from the table may look like:

| MaterialNr | Material | Pattern | cGood | cBad | cNotifs |
|---|---|---|---|---|---|
| 7563021 | D100 - Rectifier Board | GXX_2000_ERR | 6 | 1 | 7 |
| 7563021 | D100 - Rectifier Board | PRC_8_ERR | 1 | 1 | 7 |
| 7563021 | D100 - Rectifier Board | STD_9_ERR | 1 | 0 | 7 |
| 7562940 | D20 - Regulator board | STD_9_ERR | 1 | 0 | 1 |

Here, the errors that have caused the GXX_2000_ERR IBM Metric Pattern were obviated by exchanging the D100 rectifier board for a spare in six of a total of seven Notifications where this material was exchanged. The full table was input to RapidMiner for analysis to produce a bubble chart visualization of the results, shown in FIG. 3. On the x-axis are all materials where at least one Notification had a Good Patternhit. On the y-axis, are the IBM Metric Patterns. The size of the circles indicates the number of Notifications, where this pattern was a Good Patternhit for this material. The bubble chart is an indication of which IBM Metric Pattern may be a good indicator for a certain material as the cause of the failure. However, many IBM Metric Patterns have good hits for a number of different materials. Therefore, the patterns may need further refinement. To do this, errors that occurred additionally to the error of the IBM Metric Pattern were identified. By adding these additional errors to the pattern, it may be possible to more precisely determine the material that is faulty.

In Variant 2, the creation of error patterns for aborted measurements starts by extracting the aborted measurements from the MRI measurements for every Nice Notification during the four days before Notification-start and during 30 days after Notification end. Then, the errors that were reported during the aborted measurements were extracted from the MRI event logs. This list of combinations of Notifications, materials and errors is grouped by the materials identification to obtain an indication which error may be a good indicator for a certain material failure. Using this output, a bubble chart was created in RapidMiner: on the x-axis are all materials where at least one Notification had a good error; on the y-axis are all errors that were good errors for at least one Notification. The size of the circle indicates the number of Notifications, where this error is a good error for this material. The ratio between the number of Notifications where this error is a good error and the total number of Notifications for this material may be shown by the color or shading of the bubble.

The data base mining identifies which errors were apparently removed by exchanging a certain material; however, many errors were removed by several materials. To create pattern that indicate a specific material, other errors that appeared together with the good errors during the respective aborted measurements would be evaluated. This may lead to combinations of errors that indicate a specific material.

A further step was to filter all of the aborted measurements for measurement were there was at least one good error for a certain Notification. The errors that occurred during these measurements are obtained from the MRI event logs. These errors were then pivotized to yield a table with one line per aborted measurement, and the errors as columns. The following is an excerpt:

| MaterialNr | NotificationID | Serial | MRI_COH_7 | MRI_MSR_22 | MRI_MSR_23 | MRI_MSR_24 | MRI_MSR_40 |
|---|---|---|---|---|---|---|---|
| 7389195 | 400102803279 | 26159 | 1 | 1 | 1 | 0 | 0 |
| 7389195 | 400102953762 | 25980 | 0 | 0 | 0 | 1 | 0 |
| 7389195 | 400102953762 | 25980 | 0 | 0 | 0 | 1 | 0 |
| 7577906 | 4001872562 | 26494 | 0 | 0 | 0 | 0 | 1 |

| MaterialNr | MRI_PAD_22 | MRI_RFS_51 | MRI_SCT_1010 | MRI_SLO_27 | MRI_SUP_9 | MRI_SUP_440 |
|---|---|---|---|---|---|---|

-continued

| | | | | | | |
|---|---|---|---|---|---|---|
| 7389195 | 0 | 0 | 4 | 0 | 0 | 0 |
| 7389195 | 1 | 1 | 0 | 1 | 0 | 0 |
| 7389195 | 0 | 0 | 0 | 1 | 1 | 1 |
| 7577906 | 0 | 0 | 0 | 0 | 0 | 1 |

Additionally, a list of materials and their good errors is created. Note that it is also possible that there were no good errors for a material.

| MaterialNr | GoodEvents |
|---|---|
| M7389526 | MRI_GXX_29, MRI_MSR_23, MRI_MSR_24, MRI_MSR_40, MRI_PXX_3000, . . . |
| M7389542 | |
| M7389567 | MRI_COS_32, MRI_GCD_19, MRI_MSR_22, MRI_MSR_23, MRI_MSR_40, . . . |
| M7389781 | MRI_MSR_22, MRI_PAD_22, MRI_RFS_51, MRI_RFS_6, MRI_SUP_295, . . . |

Using the results of the previous actions, the combinations of errors during aborted measurements that are characteristic of a certain replaceable module were determined. That is, that whenever a combination occurred, the combination was always in a measurement that belonged to a Notification where this module was exchanged. This process is the same for both the refinement of the IBM Metric Pattern and the creation of error pattern through aborted measurements. Looking at just these four lines, the combination of errors MRI_MSR_40 and MRI_SUP_440 are characteristic for the material 7577906, but error MRI_SUP_440 alone is not sufficient to automatically determine characteristic combinations. Rapid-Miner was used. The first step in using Rapid-Miner is to create FrequentItemSets. An excerpt may be:

| Size | Support | Item 1 | Item 2 | Item 3 |
|---|---|---|---|---|
| 1 | 0.504 | MRI_MSR_24 = true | | |
| 1 | 0.226 | MRI_PXX_3000 = true | | |
| 1 | 0.224 | MRI_SUP_440 = true | | |
| 2 | 0.174 | MRI_MSR_24 = true | MRI_PXX_3000 = true | |
| 2 | 0.060 | MRI_MSR_24 = true | MRI_SUP_440 = true | |
| 2 | 0.075 | MRI_MSR_24 = true | MRI_SUP_430 = true | |
| 2 | 0.005 | MRI_MSR_22 = true | MaterialNr = M7582260 | |
| 3 | 0.002 | MRI_MSR_24 = true | MRI_PXX_3000 = true | MRI_MSR_47 = true |
| 3 | 0.002 | MRI_MSR_24 = true | MRI_PXX_3000 = true | MaterialNr = M7563021 |
| 3 | 0.002 | MRI_SUP_440 = true | MRI_MSR_22 = true | MaterialNr = M7387884 |

In this example, the error MRI_MSR_24 was present in about half of the aborted measurements and the error MRI_PXX_3000 in about 23 percent. The combination of errors MRI_MSR_24 and MRI_SUP_430 was present in 7.5 percent. Combinations with materials may also be analyzed. Using these item sets, the next step in the analysis using RapidMiner calculates association rules. The association-rule-generator takes analyzes the FrequentItemSets and determines dependencies between two or more items. For example, a result of such an analysis might look like:

[MRI_PXX_61=true]→[MRI_PXX_3000=true]
(confidence: 1.000)

That means that, on the basis of the aborted measurements, whenever the error MRI_PXX_61 occurred during one measurement, the error MRI_PXX_3000 also occurred. However, to write a pattern, rules may be selected in this example where the rule points to exactly one material. One such rule might look like this:

[MRI_GXX_19=true]→[MaterialNr=M3096260]
(confidence: 1.000)

This rule states that, on the basis of the aborted measurement event reports, whenever the error MRI_GXX_19 occurred during a measurement, there was a notification just after that error, where the material 3096260 was exchanged. For pattern generation, these rules are of interest, so the results from RapidMiner were filtered for these rules.

The output of the filtering operation is the filtered list of association rules from RapidMiner. The output contains only rules of the form:

[$ERROR_1, . . . , $ERROR _N]→[$MaterialNr]
(confidence: 1.000)

Creation of the Error pattern is of Variant 2, may start with text file from RapidMiner having information such as:

[MRI_MCO_15=true,MRI_PER_64=true]→
[MaterialNr=M7577906]

which may be interpreted as: when the error code MCO_15 and PER_64 are generated during an aborted measurement, the material with the number 7577906 was found to be defective.

The second input was a text file containing a list of materials, showing which errors appeared indicating this material. This list was used to identify the rules, where the error actually maps to a distinct material that was replaced. The list could look as follows:
M40928 MRI_PXX_3000, MRI_PXX_37
M3089208 MRI_MSR_40, MRI_SUP_430, MRI_SUP_440

The third input used was a list with stop codes:
"MRI_MSR_40", "MRI_MSR_26", "MRI_MSR_22", "MRI_MSR_24", "MRIMSR_25"

These codes were used separately to filter the relevant rules. That is, rules which contain one of those codes may be used for pattern generation. During pattern generation the stop code list may be used to identify the codes which are not part of the rule. Other rules may use the absence of particular stop codes.

When the pattern generator program module is started, the rules file was parsed and each rule stored as a line in an object consisting of a list of errors and a string variable containing the material number. This list was attached to an overall rule-list containing all rules. Since this list may be partially redundant, some rules can be eliminated from the list. Rules which are more specific than another rule, but referring to the same material and stop code may not be needed. As an example:

Error MRI_GXX_48 indicates the material 7563021 (and no other material). So the rule in the rules.txt file may looks like:

[MRI_GXX_48=true]→[MaterialNr=M7563021]

If this rule was extended by another error, but still indicating the same material (and no other), as an example:

[MRI_GXX_2001=true, MRI_GXX_48=true]→[MaterialNr=M7563021]

would be considered redundant and need not be retained.

Each rule is compared to the list of 'good events' and matched according the material identification number. The rule contains at least one error appearing in the good events list. After parsing and eliminating redundant rules, a data file for each rule-object in the rules list was created.

A ruleArray table may contain the error codes for this rule. The string material may be used for the file name, to show to which material a rules pattern refers.

The content of the ruleArray may be permutated. That is, for each permutation of a pattern a data file is created. The reason for permuting the errors (to create a pattern for each permutation) is, that one cannot generally foresee in which order the errors may appear in the log file in actual system operation.

The patterns were compared with the training data: that is, the TB notifications and IBM data that were used in the initial correlation. This will show whether the process of generating pattern is sound. Then, the patterns were examined on test data. The test data can be a portioning of the overall data set, so that data that was not used for development of the rules is used to test the efficacy of the rules: that is, Notifications that were not included in the initial correlation process. This test will show, whether the generated pattern can accurately identify materials, using the Notifications that were not available during training. Typically, there are multiple patterns that point to the same material.

To better visualize and analyze the results, the patterns are grouped by their designated materials. For example, all metric patterns that point to material number 123456 are put into the group "MP-123456" and all error patterns that point to that material were put into the group "EP-123456".

The basis for the training data included about 2400 Nice Notifications from the US and Germany between January 2008 and June 2009. The basis for the test data included about 2600 Nice Notifications from all states except the US and Germany between January 2008 and June 2009 and from all sources between July 2009 and September 2009. The bubble chart of FIG. 2 shows the performance of the error patterns using the training data from which they were derived: On the x-axis are all materials where at least one notification had a Good Patternhit. On the y-axis, are all error pattern groups that were generated and that had at least one Good Patternhit. The size of the dot indicates the number of notifications, where this pattern was a good hit for this material. The shading indicates the ratio between the number of notifications where this pattern was a good hit and the total number of Notifications for this material.

All dots marked with an X are unexpected Good Patternhits. That is, these patterns had a good hit for a material, but the material was different from the material that was expected to have been indicated by that pattern. There were only four error pattern groups with unexpected pattern hits. The cause for the unexpected Good Patternhits has been determined to be due to an error during the creation of the pattern files and not an error in the analysis.

Figure 3:
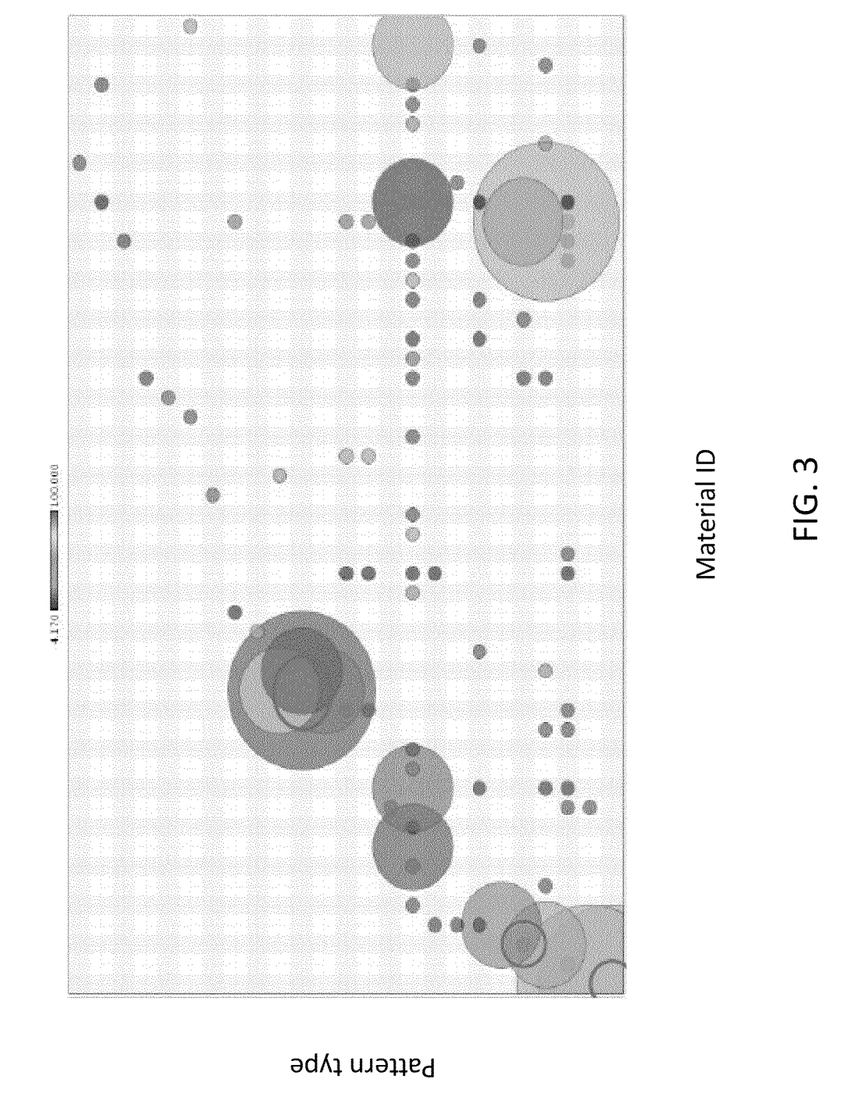
FIG. 3 is shows a bubble chart of the relationship between error message patterns and failed modules based on training with experiential data and tested against separate set of data obtained from the installed equipment base.

The bubble chart of FIG. 3 shows the performance of the error patterns using the test data: Four error pattern groups have expected Good Patternhits. The groups with the expected Good Patternhits are marked by heavy rings. In one of those groups (EP-3095700), the pattern unambiguously indicates the expected material. The error patterns appear to be significantly more stable on the training data than the metric pattern, and also show a slightly better quality on the test data than the metric pattern (not shown). The error patterns were able to identify 4 materials on the test data, whereas the metric pattern could only identify 3 materials. The analysis created metric patterns for 44 materials and error patterns for 63 materials. The relatively low number of materials that were identified with this analysis would nevertheless improve the efficiency of servicing the geographically dispersed MRI installed system base, as they may represent a proportionally greater number of failure events.

If the same material has different versions (for example computers with 8 GB RAM or 16 GB RAM) there are several material identification numbers that will likely exhibit the same behavior when they are defective. At present, the analysis addresses material with a specific identification number that exhibits a unique behavior when defective. Currently, the analysis only creates a pattern when the data indicates exactly one failed material identification in the training process. It may be useful, therefore, to define material groups having a plurality of different material numbers for replaceable material modules that are expected to produce similar error messages when a failure occurs. There may also be materials that are always changed together as a group in response to a failure one of the group. These materials are currently ignored by the analysis. Taking such groups of materials into account may cover more materials with the patterns.

Patterns that point to multiple materials have been eliminated in the present analysis; however, the results of the pattern on the test data suggest that patterns may not be created for some materials, even with reasonable hardware and software changes. However, the use of a Pattern that indicates a material with a certain probability of correctness, may permit the creation of additional patterns. For example, a pattern hit may be useful when indicating an 80% chance that a certain material must be exchanged.

The IPB Notifications that are used as training and test data are already filtered. Essentially, only notifications are considered where only one material was exchanged. The reason for the filtering in this example was to be reasonably sure that the disappearance of errors that occurred just before a Notification can be attributed to a single faulty replaceable material module. This constraint may be problematic if there are several notifications for the same MRI machine during a short period of time. The periods of time that are analyzed for these Notifications will overlap. As a consequence the analysis may wrongly attribute the appearance of a certain pattern of errors to multiple materials, with the result that no pattern will be generated for either.

Restricting the IPB Notifications further, to notifications that had no follow-up notifications for the next 30 days may permit writing patterns for materials that are outside the scope of the current analysis. But, at the same time, this approach may further restrict the overall amount of training data, which could ultimately lead to fewer patterns for fewer materials. In the examples, the MRI error data were not filtered for system types or software versions of MRI systems. There may well be significant differences in error behavior and material failure rates between them. The analysis would write two different patterns for such a situation. However, if two different kinds of systems use different modules, for example, but display the same error behavior, an error patter for either of the materials may be difficult to uncover. This could be mitigated by partitioning the training data by MRI system type or software version and conducting separate analyses for each case. Generally, as the number of error reports in the data base increases, the data base can be further segmented so as to be more particular to an equipment configuration, while having sufficient data for useful analysis.

The examples did not take account of the physical and functional interrelationships of the components of the system. Being a complex system, the error messages may not have been originally designed as diagnostic of hardware failures of a specific type but, rather, of a failure of the MRI system to properly perform the MRI scan in a safe and satisfactory manner. For example, a failure in a RF connector or cable, may be represented by a failure in receiving RF energy; however, this failure may be due to the RF generator, the cable, the connector, the receiving antenna, or the receiver. Unless error messages can be related directly to a measurable performance attribute of the individual module, the result may be ambiguous. So, for example, the grouping of modules into subsystems having a known functional relationship as an intermediate step in the identification of the failed material may improve localization of the failed module. Moreover, such decision analysis may be further refined by taking account of the experiential failure rates of the individual module types of such groupings of modules.

The patterns need not all be derived from data mining; where specific engineering knowledge, or failure rates, or the like, are evidently useful to identify a failed module or needed adjustment or calibration with a event report, such rules may be constructed in a heuristic manner and added to the pattern set.

As a system design tool, improvements to the design of the equipment and the error messaging scheme may be initiated based on a determination of modules for which the present analysis suggests that the performance measurements upon which error messages are currently generated do not adequately distinguish the failed module. This would be either a part of new system design, or a process of continuous improvement driven by the mined data of the IPB.

In an aspect, a method of servicing an installed base of complex systems may include the collection of error reports of all types generated by the system, and reports of the replacement of failed modules by a specific service performed. The data base thus constructed may be subject to data mining operations so as to uncover the relationships or patterns relating the error messages to specific hardware failures or adjustments needed to restore the system to proper operation.

After the patterns have been generated and validated, new error messages may be compared against the patterns to determine if a match between a generated pattern and the new error message pattern has occurred. Where a match between the error messages and a pattern is identified, the failed material or other service action associated with the error messages, may be retrieved from a data base and displayed for use. A repair part may be retrieved from inventory and either sent to the site of the failed system, or be brought to the site by an appropriately trained technician.

In another aspect, where failed materials cannot be identified by the existing pattern set, the individual part numbers of the replaced modules may be reported to product engineering so that consideration of redesign of the hardware or software of the system may be undertaken so as to improve the serviceability.

In yet another aspect, the method may include updating the installed product data base so as to include error messages and service reports that occur on a continuing basis. These additional data may be subject to a data mining operation so as to improve the quality of the rules. For example, where the failure rate of a particular module is comparatively very low, the occurrence of sufficient failures to make the identification of a pattern by data mining may take some time to accumulate in the data base. Such failures, while infrequent, would be useful to identify, as the very low failure rate makes it less likely that a service technician would consider the failure to have occurred, and the identification of the failed module may be delayed.

While the methods disclosed herein have been described and shown with reference to particular steps performed in a particular order, it will be understood that these steps may be combined, sub-divided, or reordered to from an equivalent method without departing from the teachings of the present invention. Accordingly, unless specifically indicated herein, the order and grouping of steps is not a limitation of the present invention.

Figure 4:
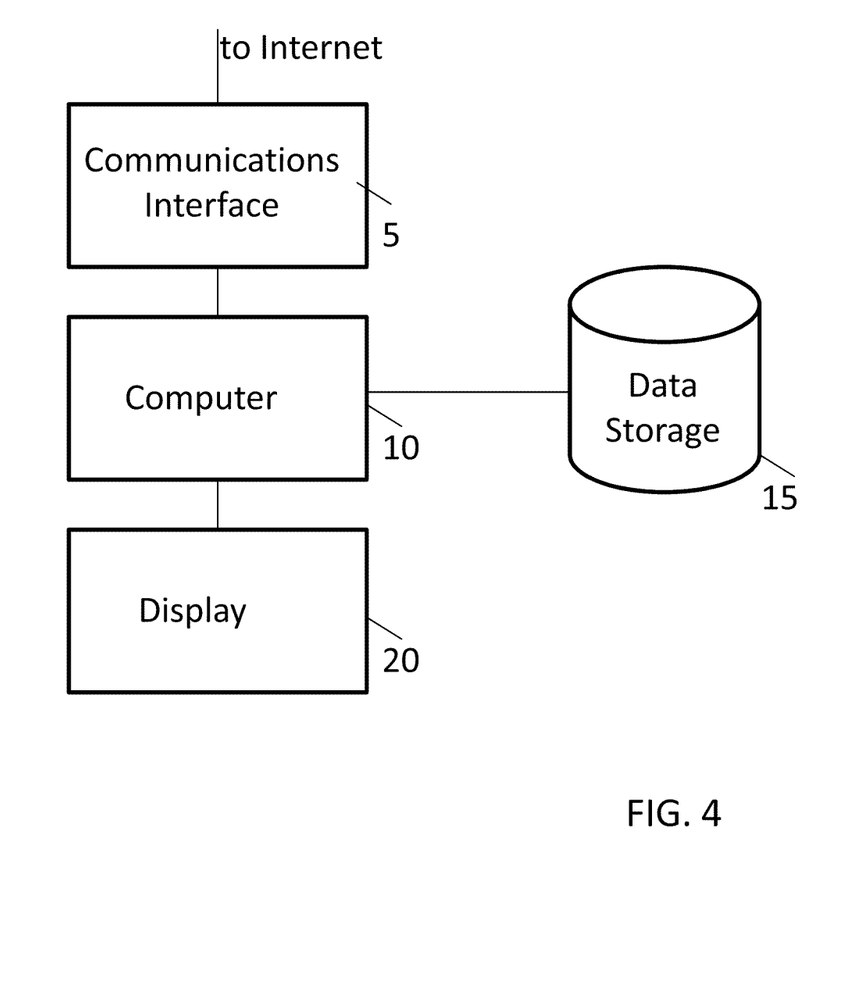
FIG. 4 is a block diagram of a system for performing a method of servicing the installed equipment base.

A system for performing the functions associated with the methods of managing the servicing of the geographically dispersed equipment is shown in FIG. 4. A computer 10 may be configured to perform the functions of accepting error messages received, for example, over a communications interface 5, and storing the data on a non-volatile storage medium 15. The stored data may be formatted and analyzed so as to provide the error patterns for evaluating subsequent error reports so as to identify service events for which known responses are available. A report may be output to a display 20 or to another location through the communications interface 5.

Although only a few examples of this invention have been described in detail above, those skilled in the art will readily appreciate that many modifications are possible without materially departing from the novel teachings and advantages of the invention. Accordingly, all such modifications are intended to be included within the scope of this invention as defined in the following claims.

What is claimed is:

1. A system for managing the servicing of a geographically separated installed base of equipment, the system comprising:
    an interface configured to receive, over a wide area network, one or more error reports from the geographically separated installed base of equipment;
    a processor geographically remote from the geographically separated installed base of equipment, the processor configured to store the one or more error reports as a data base on a non-volatile medium; and
    a data miner configured to process the data base containing the one or more error reports and to formulate an error pattern rule indicating a failure to be the subject of a service event, wherein formulation of the error pattern rule comprises a variant of pattern generation selected from the group consisting of a metric pattern variation and an error pattern variation;
    wherein the geographically remote processor is configured to compare a currently received error report with the error pattern rule and output a notification of the service event when a match between the currently received error report and the error pattern rule occurs, and wherein the service event notification output includes a location of equipment of the geographically separated installed base of equipment to be serviced and a hardware module to be replaced, an adjustment to be performed, a diagnostic procedure to be performed at the location of the equipment to be serviced, or a combination thereof.

2. The system of claim 1, wherein the wide area network is the Internet.

3. The system of claim 1, wherein the error pattern rule is a plurality of error pattern rules including error pattern rules resulting from data mining and from heuristic analysis.

4. The system of claim 1, wherein the service event notification output includes an identification of a plurality of hardware modules to be evaluated at a location of equipment of the geographically separated installed base of equipment, from which the currently received error report was received.

5. The system of claim 1, wherein the service event notification output includes a request to the equipment of the geographically separated installed base of equipment for error reports stored locally at the location of the equipment.

6. The system of claim 1, wherein the processor is further configured to identify and store error reports that do not result in a match to the error pattern rule.

7. A method of servicing geographically dispersed equipment, the method comprising:
   receiving an error report over a wide area network from the geographically dispersed equipment;
   storing the error report in a non-volatile data base;
   operating a computer configured to perform data mining of a plurality of error reports in the data base to produce error pattern rules indicative of a specific failure type, the plurality of error reports comprising the error report, the computer being geographically remote from the geographically dispersed equipment;
   comparing a subsequent error report received from equipment of the geographically dispersed equipment with the error pattern rules to determine when a match between the subsequent error report and a rule of the error pattern rules occurs; and
   outputting, with the geographically remote computer, a report when the match occurs, the report including specific equipment of the geographically dispersed equipment and a specific failure type associated with the matched rule;
   wherein the specific failure type is associated with an adjustment to be performed at a location of the specific equipment, a diagnostic test to be performed at the location of the specific equipment, or a combination thereof; and
   wherein formulation of the error pattern rules comprises a variant of pattern generation selected from the group consisting of a metric pattern variation and an error pattern variation.

8. The method of claim 7, wherein the specific failure type is associated with a replaceable hardware module.

9. The method of claim 7, wherein the computer is further configured to store data, the data comprising error reports and an identification of hardware modules that are replaced without being identified with an error pattern rule of the error pattern rules, wherein the stored data includes a time stamp relating to a time of an event or a time of the replacement.

10. The method of claim 7, wherein the output report includes a specific hardware module to be retrieved from an inventory location.

11. The method of claim 10, wherein the inventory location, a location of the equipment and a location of the computer are different locations.

12. A computer program product comprising:
   instructions stored on a non-transitory computer-readable medium, the instructions operable to configure a computer to:
      receive error reports over a wide area network from geographically dispersed equipment, the computer being geographically remote from the geographically dispersed equipment;
      store the error reports in a non-volatile data base;
      perform data mining of the error reports to produce error pattern rules indicative of a specific failure type;
      compare a subsequently received error report with the error pattern rules to determine when a match between the error report and a rule of the error pattern rules occurs; and
      output a report when the match occurs, the report including specific equipment of the geographically dispersed equipment and the specific failure type associated with the matched rule;
   wherein the report includes an identification of a hardware module to be replaced, an adjustment to be made to the specific equipment, a diagnostic routine to be performed on the specific equipment, or a combination thereof; and
   wherein formulation of the error pattern rules comprises a variant of pattern generation selected from the group consisting of a metric pattern variation and an error pattern variation.

* * * * *